(12) United States Patent
Hillegas et al.

(10) Patent No.: US 6,214,618 B1
(45) Date of Patent: Apr. 10, 2001

(54) MICROCARRIER BEADS HAVING A STYRENE COPOLYMER CORE AND A COVALENTLY LINKED TRI-METHYLAMINE EXTERIOR

(75) Inventors: William J. Hillegas; David E. Solomon, both of Ann Arbor; Gilbert H. Wuttke, Saline, all of MI (US)

(73) Assignee: Solohill Engineering, Inc., Ann Arbor, MI (US)

( * ) Notice: Subject to any disclaimer, the term of this patent is extended or adjusted under 35 U.S.C. 154(b) by 0 days.

(21) Appl. No.: 09/287,793

(22) Filed: Apr. 7, 1999

Related U.S. Application Data
(60) Provisional application No. 60/080,992, filed on Apr. 7, 1998.

(51) Int. Cl.$^7$ .............................. C12N 5/00; C12N 5/02; C12N 5/06; C12N 5/08; C12N 11/08
(52) U.S. Cl. ..................... 435/396; 435/177; 435/180; 435/395; 435/403
(58) Field of Search ..................................... 435/174, 176, 435/177, 180, 395, 396, 403

(56) References Cited

U.S. PATENT DOCUMENTS

| | | | |
|---|---|---|---|
| 4,191,814 | 3/1980 | Amick | 521/32 |
| 4,252,644 | 2/1981 | Small et al. | 210/656 |
| 4,273,878 | 6/1981 | Amick | 521/32 |
| 4,994,388 | 2/1991 | Hillegas et al. | 435/402 |
| 5,114,855 | 5/1992 | Hu et al. | 435/403 |
| 5,679,229 | 10/1997 | Goldstein et al. | 204/524 |

OTHER PUBLICATIONS

Chen, Hsiu–mei, et al., Effect of replacing helical glycine residues with alanines on reversible and irreversible stability and production of *Aspergillus awamori* glucoamylase, (1996), Protein Engineering, 9:499–505.

Gebb, Christine, et al., Alternative Surfaces for Microcarrier Culture of Animal Cells, (1982), Develop. Biol. Standard., 50:93–102.

Giard, Donald J., et al., Virus Production with a Newly Developed Microcarrier System, (1977), Applied and Environmental Microbiology, 34:668–672.

Keese, Charles R., et al., Cell Growth on Liquid Microcarriers, (1983), Science 219:1448–1449.

Nielsen, V., et al., Biosilon ®, Optimal Culture Conditions and Various Research Scale Culture Techniques, (1980), Develop. Biol. Standard., 46:131–136.

Obrenovitch, Angele, et al., Microcarrier culture of Fibroblastic Cells on Modified Trisacryl Beads, (1982), Biol. Cell, 46:249–256.

Sambrook, J., et al., Molecular Cloning: A Laboratory Manual, Second Edition, (1989, 1992), Cold Spring Harbor Laboratory Press, New York.

Varani, James, et al., Growth of Three Established Cell Lines on Glass Microcarriers, (1983), Biotech. and Bioengin., 25:1359–1372.

Varani, James et al., The effect of substrate on the production of infectious virus by cells in culture, (1988), J. Biol. Standard., 16:333–338.

Varani, James, et al., Cell growth on microcarriers: comparison of proliferation on and recovery from various substrates, (1986), J. Biol. Standard., 14:331–336.

Varani, James, et al., Substrate–Dependent Differences in Production of Extracellular Matrix Molecules by *Squamous Carcinoma* Cells and *Diploid Fibroblasts*, (1989), Biotech. and Bioengin., 33:1235–1241.

Varani, James et al., Use of recombinant and synthetic peptides as attachment factors for cells on microcarriers, (1993), Cytotechnology, 13:89–98.

Varani, James, et al., Human diploid fibroblast growth on polystrene microcarriers in aggregates, (1996), Cytotechnology, 22:111–117.

Van Wezel, A.L., Growth of Cell–strains and Primary Cells on Micro–carriers in Homogenous Culture, (1967), Nature, 216:64–65.

*Primary Examiner*—David M. Naff
(74) *Attorney, Agent, or Firm*—Kohn & Associates

(57) ABSTRACT

There is provided a method of making microcarrier beads having the steps of forming a bead made of a lightly crosslinked styrene copolymer core and also having functional groups on the surface of the bead and washing the microcarrier beads with basic and acidic solutions to make the beads compatible for cell culture. Also provided is a microcarrier bead made of a styrene copolymer core with a tri-methylamine exterior which has been washed in basic and acidic solutions to make the beads compatible for cell culture. The method of using microcarrier beads for increased growth of anchorage dependent cells having the steps of washing the microcarrier bead with basic and acidic solutions and mixing the microcarrier bead with an anchorage dependent cell containing culture medium is also provided.

13 Claims, 3 Drawing Sheets

MICROCARRIER BEADS HAVING A STYRENE COPOLYMER CORE AND A COVALENTLY LINKED TRI-METHYLAMINE EXTERIOR

CROSS REFERENCE TO RELATED APPLICATIONS

This application is based on U.S. Ser. No. 60/080,992 filed Apr. 7, 1998 which is incorporated herein by reference.

GOVERNMENT SUPPORT

DHHS/PHS/National Cancer Institute #2R44CA74595

BACKGROUND OF THE INVENTION

1. Field of the Invention

This invention relates generally to systems for culturing cells. More particularly, the invention relates to a tri-methylamine (TMA) microcarrier bead system which serves as a microcarrier support for the culturing of anchorage-dependent cells.

2. Description of Related Art

The use of microcarrier supports to facilitate growth of biological cells has a long and varied history. Early systems for effecting such cell growth in useable quantities have included the well-known petri dish and flasks. Efforts intended to increase the quantity of cell production have resulted in the use of large trays. The overall effect achieved being the increase in the surface area on which the biological cells are grown, specifically anchorage-dependent cells. Some of these early cell-growth systems are still in use for applications where small-scale, high labor content cell culture systems will suffice, such as in hospital and university research units.

The state of the cell culturing art has continued to develop to the present day where there is an acute need for large scale, low labor content, commercial cell culturing systems which can achieve high rates of production. Ideally, the production rate should be flexible to accommodate batch and single order production.

At present, the cell culturing system which enjoys utilization in some 60% to 80% of the commercial market is the roller bottle system. Essentially, a roller bottle is a cylindrical container which is arranged to contain a small amount of nutrient media. In operation, the roller bottle is rotated slowly about its longitudinal axis, at about 1 to 3 rpm, whereby the nutrient media is continually caused to wet the entire interior surface of the bottle, on which cell growth is achieved. A plurality of such roller bottles are operated on a roller rack, the specific number thus rotated being responsive to the desired rate of overall cell production.

The remaining 20% to 40% of the commercial large scale market utilizes microcarrier systems. Although other techniques have been introduced in recent years, including hollow fibers, fiber bundles, cell growth cubes, and channeled ceramic cores, only microcarrier systems have the potential to achieve anchorage dependent cell growth at commercially advantageous production rates with low labor content. Achieving large scale in this manner is superior to achieving it by replication, as is the case with roller bottles and other known systems. In addition, microcarrier bioreactor systems are well-suited for automated large scale cultivation of anchorage dependent cells.

As is evident from Table 1 below, several microcarrier systems are presently commercially available. This table summarizes some of the characteristics of the commercially available microcarriers, including polystyrene, glass-coated polystyrene, and the novel TMA microcarriers of the present invention.

The British-based company, Amersham-Pharmacia-Biotech, was the first to introduce the microcarrier bead in the early 1970's. Subsequently, this company has acquired about a 90% share of the microcarrier bead market, worldwide.

The use of microcarrier beads as the microcarrier elements in anchorage dependent cell production systems requires the availability of bioreactors, support equipment, and a stirring system. The system elements interact with one another to maintain the cell-laden microcarrier beads in suspension in the nutrient media. Much of this type of equipment is commercially available, and the effort to develop and improve bioreactor systems for use with microcarrier beads has intensified.

Current microcarrier use in the large-scale cultivation of anchorage dependent cells. Large scale cultivation of anchorage dependent cells is done primarily for the production of vaccine strain viruses used in human and animal medicine. Genetically engineered biological production has recently begun use of large scale, cell culture technologies. Two additional uses, production of virus vectors for gene therapy and production of specific cell types for cellular therapies, will utilize the same technologies in the future. Nothing in the foreseeable future is likely to reduce the need for large quantities of anchorage dependent cells. In the past, roller bottles have been the most extensively used technology in large scale cell culture operations. More recently, other technologies including hollow fiber culture systems and microcarrier/bioreactor systems have replaced roller bottles in some applications. Both technologies have certain advantages over roller bottles which will likely make this trend continue. Hollow fiber reactors are useful for growing anchorage independent cells (e.g., mainly hybridomas for antibody production), but are not optimal for large-scale cell culture operations. Microcarrier/bioreactor systems offer the best alternative to roller bottles for the large-scale cultivation of anchorage-dependent cells with a low labor content.

Microcarrier development started in 1967 when van Wesel demonstrated that DEAE—dextran beads could be used as a substrate for the growth of anchorage-dependent cells in a suspension culture mode (Van Wezel (1967). Since that time, a number of different materials including glass, polystyrene plastic, acrylamide, solid collagen, porous collagen, cellulose and liquid fluorocarbons have been successfully used as microcarriers (Varani, et al. (1983); Nielson, et al. (1980); Obrenovitch, et al. (1982); Giard, et al., (1977); Gebb, et al., (1982)). In addition, microcarriers with one or more adhesive peptides attached to the surface through covalent or noncovalent linkages have been used (Keese, et al. (1983); Varani, et al. (1988); Varani, et al., (1986)). To be useful as a microcarrier, a material must have a surface chemistry which supports cell attachment and growth, and must not be toxic to the cells or to the elaborated products. The ideal microcarrier should have a diameter of approximately 75–225 μm, although larger or smaller sizes (U.S. Pat. No. 5,114,855 (May 1992); J. Varani, S. Josephs and W. Hillegas, "Human Diploid Fibroblast growth in polystyrene microcarriers in aggregates", Cytotechnology, 22: 111–117 (1996)) have been used. The ideal density appears to be in the range of 1.02–1.05 g/cc, although lighter or heavier material may be better suited for certain applications. In addition to differences in surface chemistry, microcarriers made from one substance or another differ in such characteristics as rigidity, porosity and adsorptive capacity. Differences in handling characteristics, durability, shelf-life and ease of sterilization all distinguish one substance from another as does overall manufacturing costs. From the standpoint of commercial potential, all of these variables must be considered.

Although a large number of different types of material have been developed for use as microcarriers, only two types of microcarrier products are widely-used in the industry today. These are the i) dextran-based microcarriers (Cytodex I, DEAE-dextran; and Cytodex III, porcine collagen-coated dextran) made in Sweden and sold by Amersham-Pharmacia Biotech of the United Kingdom and ii) the coated polystyrene based microcarriers made in the United States by SoloHill. Microcarriers made by SoloHill have been successfully integrated into manufacturing processes in the United States, Europe and Japan. SoloHill makes a porcine collagen-coated polystyrene microcarrier bead, which is heavily used in the animal health industry to produce viral vaccines. Smaller amounts of Solohill's glass-coated polystyrene microcarriers have also found a use in industry, and an intense interest has developed in the recently-released ProNectin F*—coated polystyrene beads, largely because they are free of animal proteins. (*ProNectin F is a genetically engineered protein incorporating multiple copies of the cell attachment ligand (RGD) from fibronectin. It is available from Protein Polymer Technologies, Inc..)

However, the entire viral vaccine industry appears to be on the cusp of a revolution, in which virtually every existing protocol will come into question. This is due largely to concerns about bovine spongiform encephalopathy (BSE), the "mad cow" disease, in the food chain and the attendant effort to eliminate animal-derived proteins from manufacturing processes. One focus is on replacement of serum-containing culture media with fully synthetic media. However, as serum containing media are eliminated, there will be no tolerance for substrates containing bovine or porcine collagen or any other animal protein. As indicated above, most manufacturing procedures that use microcarriers use either the collagen-coated dextran beads (Amersham-Pharmacia Biotech) or the collagen-coated polystyrene beads produced by SoloHill. The push to eliminate animal proteins from vaccine manufacturing thus provides an opportunity for wide evaluation of a novel, animal protein-free substrate such as the TMA microcarriers. The European regulatory agency (EMEA), it should be noted, has already begun a strong effort to remove animal-derived proteins from biological product manufacturing. In the United States, the FDA issued an "advisory" on May 9, 1996 the inference of which is that manufacturers should move expeditiously to eliminate animal proteins from their processes stating "We strongly recommend you take whatever steps are necessary to assure yourselves and the public that, in the manufacture of FDA-regulated products intended for administration to humans, you are not using materials that have come from cattle born, raised, or slaughtered in countries where BSE is known to exist. FDA believes that immediate and concrete steps must be taken by manufacturers to reduce the potential risk of human exposure to, or transmission of, the infectious agent which causes BSE in cattle."

It would therefore be useful to develop a microcarrier system which does not contain animal proteins.

SUMMARY OF THE INVENTION

According to the present invention, there is provided a method of making microcarrier beads having the steps of forming a bead made of a lightly crosslinked styrene copolymer and also having functional groups on the surface of the bead and washing the microcarrier beads with an acidic solution to make the beads compatible for cell culture. Also provided is a microcarrier bead made of a styrene copolymer with a tri-methylamine exterior which has been washed in a chemical solution to make the beads compatible for cell culture. The method of using microcarrier beads for increased growth of anchorage-dependent cells having the steps of washing the microcarrier bead with an acidic solution and mixing the microcarrier beads with an anchorage-dependent cell containing culture medium is also provided.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1A:
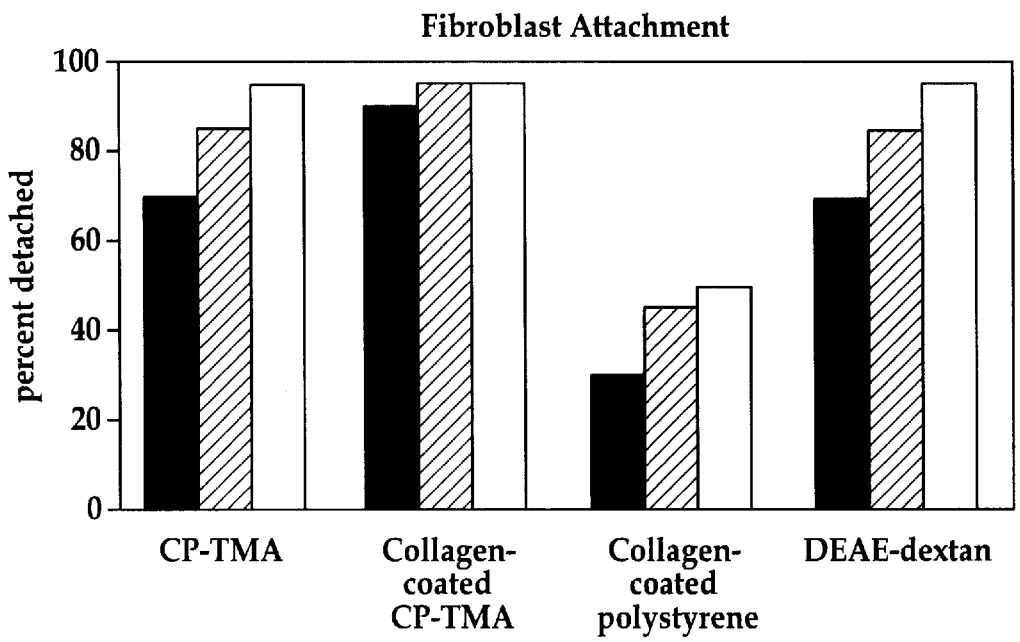
FIGS. 1A–D are graphs showing the attachment and spreading of MDCK cells (B and D) and human diploid fibroblasts (A and C) on microcarriers consisting of TMA, collagen coated polystyrene and DEAE-dextran.
Figure 1B:
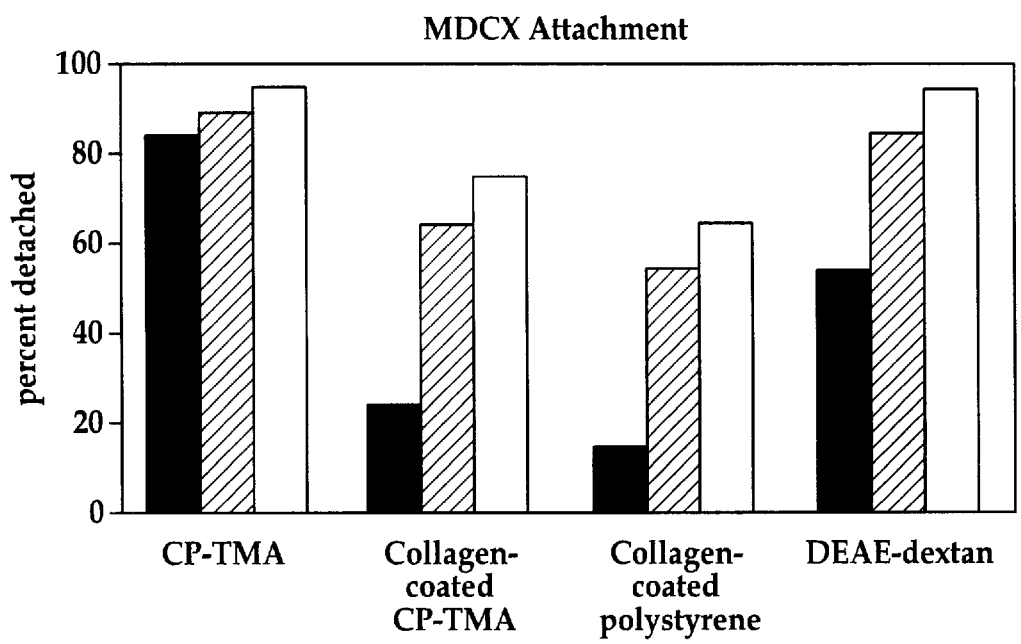
Figure 1C:
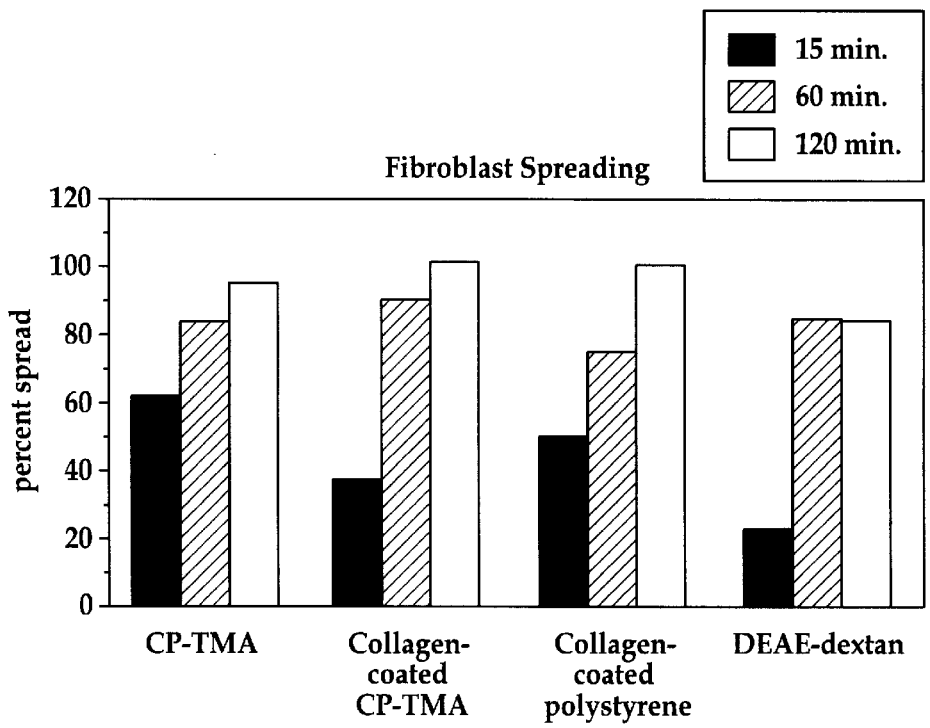
Figure 1D:
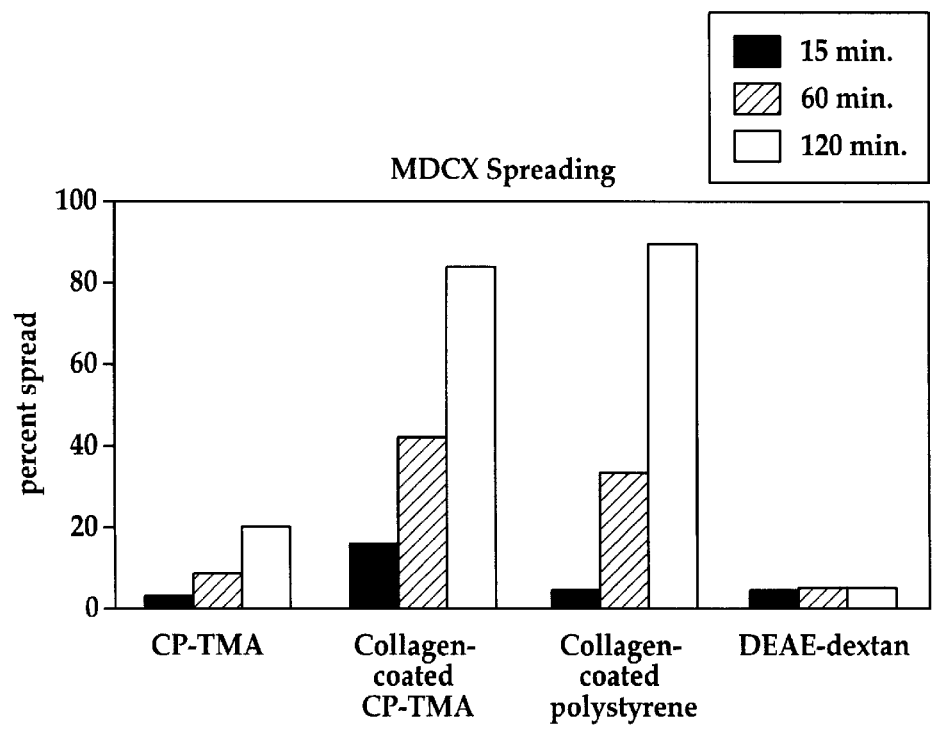

The method of making the microcarrier beads includes making the beads from a lightly crosslinked styrene monomer core with divinyl benzene and tri-methylamine attached to the surface of the bead. This bead remains autoclavable and provides a better cell binding surface. By utilizing this combinatorial chemistry and lower crosslinking, cells are more readily adherent than when cells are on totally solid surface beads. The TMA functional group which is on the surface of the bead is a cationic amine. The cationic amine is covalently linked to the surface of the bead and facilitates cell attraction and attachment.

Additionally, the TMA microcarrier bead can be further coated, if important to a specific cell culture. This coating can include, but is not limited to, porcine, bovine or human collagen, or ProNectin-F, (a recombinant fibronectin-like moiety) or other natural or synthetic peptides. This coating is applied in the same manner as is utilized for standard collagen-coated polystyrene microcarriers (See U.S. Pat. No. 4,994,388 to Hillegas et al.).

In another embodiment of the present invention, a t-butyl styrene core crosslinked with divinyl benzene is utilized. After the copolymer core is formed, a TMA exterior is added, thus giving the bead a 1.04 specific gravity whereas the styrene monomer based core would have a specific gravity of about 1.1. As stated previously, this TMA surface is cationic, is bonded to the surface of the bead, and facilitates cell attraction.

Further, as detailed above, the microcarrier bead made with a t-butyl styrene core can be further coated if important to cell culture. This coating can include, but is not limited to porcine, bovine or human collagen, or ProNectin F, a recombinant fibronectin, or other natural or synthetic peptides. This coating is applied in the same manner as is utilized for standard collagen-coated polystyrene microcarriers. (See U.S. Pat. No. 4,944,388 to Hillegas, et al.).

The method of making the microcarrier beads also includes washing the microcarrier beads with chemical solutions, such as basic-acidic solutions. More specifically, this chemical treatment includes washing the microcarrier beads first with a basic solution. Then, the microcarrier beads are rinsed with deionized water until a neutral pH is reached. After reaching a neutral pH the microcarrier beads are washed in acidic solution. Next, the microcarrier beads are rinsed with water until a neutral pH is again reached. Finally, the microcarrier beads are air dried. This overall process creates a microcarrier bead with a microporous surface, thus enabling faster attachment of cells during cell culture.

In a preferred embodiment, the range of the microcarrier bead diameter is between 75 and 225 micrometers. Additionally, the preferred microcarrier bead has the density in the range of 1.04 to 1.1 g/cc. While these are the preferred embodiments, additional size beads or beads made of heavier material may be suited for certain applications.

In another embodiment of the present invention, the microcarrier bead has a t-butyl styrene back bone. By utilizing a t-butyl styrene back bone, the density of the microcarrier bead is significantly lowered. This lowered density reduces problems which can arise relating to shear forces that occur while stirring the higher density microcarrier beads at higher speed in the nutrient media. During higher speed stirring to keep the higher density beads in suspension, turbulence in the nutrient media impose forces upon the cells under development. The cells are so fragile that these forces may damage them and reduce their proliferation. The obvious answer to this problem is to reduce the shear forces by slowing the stirring system and this requires the lower density achievable with t-butyl styrene.

Also, there is provided a method of using the microcarrier beads to increase the growth of anchorage dependent cells in a cell containing culture medium. The mixture of the microcarrier bead and the anchorage-dependent cell containing culture medium must be continuously stirred in order to maintain contact between the microcarrier beads and the cells in the culture medium. After the mixture has been stirred for a sufficient time, as can be determined by one skilled in the art, the culture medium is removed from the container. Then the anchorage-dependent cells must be removed from the microcarrier bead. This is accomplished by washing the microcarrier bead with a solution. The preferred solution is EDTA or other commonly used cell dissociation solutions.

As stated previously, the present invention utilizes microcarrier beads which have a micro-porous surface. This micro-porous surface appears to provide stronger attachment of cells to the microcarrier bead through the extension of filipodia from the cells.

The above discussion provides a factual basis for the use and manufacture of microcarrier beads. The methods used with and the utility of the present invention can be shown by the following non limiting examples and accompanying figures.

EXAMPLES

General Methods
General methods in Molecular Biology

Standard molecular biology techniques known in the art and not specifically described were generally followed as in Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Md. (1989).

Example 1
Synthesis of Tri-Methylamine Microcarriers

As indicated above, most cell types rapidly attach to dextran-based microcarriers but spreading of the attached cells is slow. In contrast, cell attachment to polystyrene microcarriers is slower but cells that do attach spread. Since both attachment to the substrate and spreading are prerequisites for entry into the proliferative cycle, the ideal substrate should support both events. The data presented indicate that the tri-methylamine (TMA) microcarriers may be the ideal substrate for both events. These microcarriers consist of styrene core, lightly crosslinked, and with a TMA exterior surface. The current microcarriers consist of a highly crosslinked, rigid styrene core. The lightly crosslinked bead, while still autoclavable, will swell by absorbing the aqueous media. This feature permits the cells to be observed more readily than on the totally rigid beads. The TMA functional group, a cationic amine, is covalently linked to the surface and facilitates cell attraction in a manner similar to other commonly used cationic amines [e.g., polylysine, polyethylenimine or diethylaminoethyl (DEAE)]. These microcarrier beads, which are referred to as tri-methylamine (TMA) microcarriers, can then be further coated with porcine, bovine or human collagen or ProNectin-F, a recombinant fibronectin, or other natural or synthetic peptides in the same manner as standard collagen-coated polystyrene microcarriers, if important to the cell culture application. (See U.S. Pat. No. 4,994,388 to Hillegas et al.)

Adhesive Characteristics of TMA Microcarriers

In the initial experiments, capacity of the TMA microcarriers to support attachment and spreading of two different cell types was assessed. For these experiments, the standard, 2-ml static culture assay was used. In this assay, replicate 35-mm (diameter) plastic culture dishes containing enough microcarriers to provide approximately 30 $cm^2$ of surface area are seeded with 2.5–5×$10^5$ cells. Cells and microcarriers are mixed by gentle trituration at time-zero and by gentle agitation of the dishes at 15 minute intervals over the first two-hour period. Cell attachment to the microcarriers and cell-spreading are assessed at various times. Attachment is determined by separating the microcarriers with attached cells from the nonattached cells and making direct counts of the cells after removal from the microcarriers with trypsin/EDTA. Cell spreading is assessed microscopically. It has been demonstrated in a number of past reports that while the 2-ml static cultures do not mimic suspension cultures exactly, the data obtained in these small scale cultures is consistent with what is seen in the larger, stirred-tank cultures (Varani, et al. (1983); Varani, et al., (1989); Varani, et al., (1993)).

FIG. 1 demonstrates attachment and spreading characteristics of two different cell types [e.g., human diploid fibroblasts and Madin Darby Canine Kidney (MDCK) epithelial cells] on the TMA microcarriers (with or without additional collagen-coating). Comparative data using Swedish made Cytodex I (DEAE-dextran) microcarriers and SoloHill—made collagen-coated polystyrene microcarriers are also shown. This figure shows that both the diploid fibroblasts and epithelial cells attach rapidly to the copolymer/TMA microcarriers. In the attachment assay, these two substrates behave in a similar manner to DEAE—dextran microcarriers. Attachment is more rapid than on collagen-coated polystyrene microcarriers. On the other hand, the TMA microcarriers are similar to the collagen-coated TMA microcarriers in that cells rapidly spread once they are attached. This is particularly true for the collagen-coated TMA microcarriers. Thus, in regard to initial attachment and spreading, the TMA microcarriers appear to combine the best features of both the DEAE-dextran carriers and the collagen-coated polystyrene beads.

Figure 2:
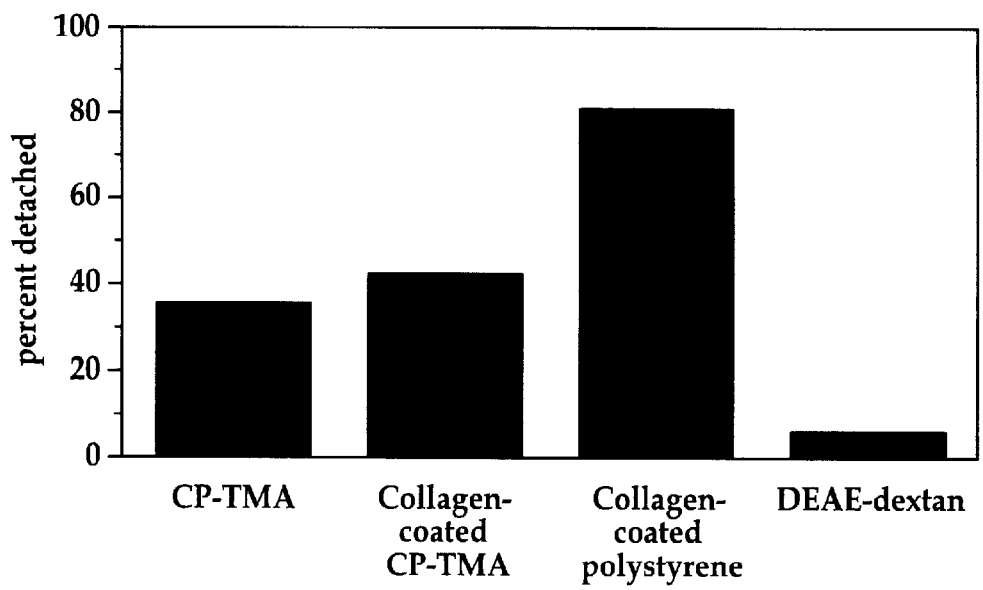
FIG. 2 is a graph showing sensitivity of MDCK cells to trypsin/EDTA-mediated release for microcarriers consisting of TMA, collagen-coated polystyrene and DEAE-dextran.

As part of these studies, the issue of cell retrieval from the substrate was addressed. As indicated above, difficulty in removing viable cells from dextran-type microcarriers is a characteristic feature of this material. Since the TMA microcarriers behave like dextran-type microcarriers in attachment characteristics, it was important to determine if detachment characteristics would also be the same. To assess this, diploid fibroblasts and MDCK epithelial cells were grown for 24 hours on the TMA microcarriers in replicate culture dishes. At the end of the incubation period, the culture medium was removed and a solution of 0.25% trypsin/0.2% EDTA was added to the wells. Cell detachment from the substrate as a function of time was then measured. As shown in FIG. 2, MDCK cells were readily released by the trypsin/EDTA solution. Further, it was found that virtually all of the harvested cells rapidly reattached and spread on plastic culture dishes, indicating that the cells were released in a viable state. Similar results were obtained with fibroblasts.

Cell Growth on TMA Microcarriers

As part of these initial studies, 2-ml cultures were maintained for three days. Evaluation of the cultures at the end of this period indicated a lack of toxicity. Furthermore, cell counts made after three days showed a net increase in cells. Based on the initial results, subsequent studies were performed in 100-ml stirred-vessel cultures. In this culture system, 200-ml capacity, bulb stirred culture vessels are inoculated with an equivalent amount of microcarriers in a 100-ml volume and equilibrated at 37 C and 5% $CO_2$ for two hours. Cells are then added ($2.5 \times 10^5$ per ml) under continuous stirring. Stirring speed is kept at the minimum required to keep the cells and microcarriers in suspension. Samples are taken periodically and cell attachment and spreading are assessed as in the small scale cultures. The same culture conditions have been utilized to evaluate a variety of different microcarrier substrates (2,10,11). The 100-ml suspension culture system precisely models variables that are important in larger (industrial) scale cultures.

Figure 3:
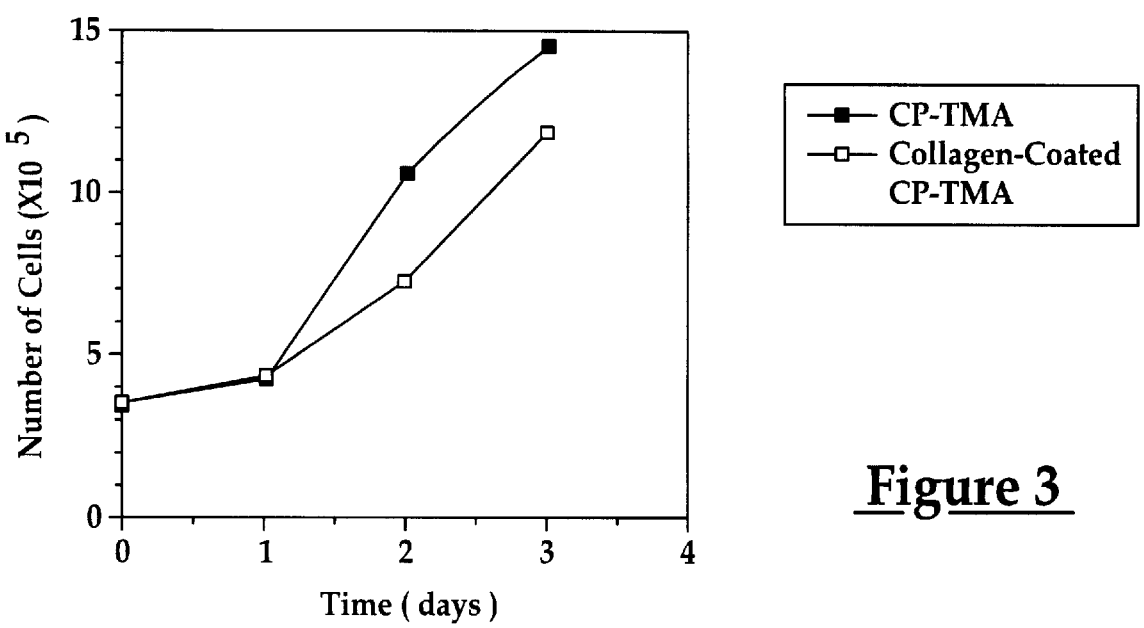
FIG. 3 is a graph showing the proliferation of MDCK cells on TMA and collagen-coated polystyrene microcarriers.

FIG. 3 shows attachment data and growth data for MDCK cells on TMA microcarriers in the 100-ml suspension cultures. As predicated by the small-scale assays, the cells rapidly attached to and spread on the substrate. These results in the 100-ml stirred vessel cultures suggest that attachment and spreading of cells will not be compromised by the high shear force present under these conditions. Furthermore, cell growth occurred such that cell numbers had increased from $3 \times 10^5$ per ml to over $1.2 \times 10^6$ per ml on both the uncoated TMA microcarriers and the collagen-coated TMA microcarriers. Finally, it was found that cell detachment from the substrate was readily achieved with trypsin/EDTA and that a high percentage of the detached cells (>95%) were capable of replating.

Summary of Findings

In summary, these findings show that the TMA microcarriers combine the best features of both the dextran-type microcarriers and the polystyrene microcarriers. Based on this, these microcarriers will provide a product to successfully function where standard collagen-coated microcarriers are unsuited. Further, the unique properties of this novel microcarrier allows use of the microcarrier in areas for which no present microcarrier is satisfactory. This extends the advantages of microcarrier/bioreactor technology to processes that are still tied to roller bottles.

Example 2

Another inroad for the TMA microcarriers is in applications that currently use serum containing medium in conjunction with roller bottles. Many of the cells used in these procedures will not adhere to the tissue culture treated polystyrene effectively when serum-free medium is used in place of serum-containing medium. If a highly-adhesive microcarrier product such as the TMA microcarriers were to become commercially available, it will provide the impetus for conversion of applications from a roller bottle mode to a microcarrier/bioreactor culture system.

There is another use for products like the TMA microcarriers. One is in the production of avian virus vaccines (.e.g., turkey herpes virus vaccine for Marek's disease). The other is in the production of genetically-engineered biologicals. In the production of the Marek's disease vaccine, an excess of chick embryo fibroblast-like (CEF) cells is added to the substrate. A very short attachment period is followed by inoculation with virus-infected cells. Efficient virus production depends on the rapid attachment of cells to the substratum and spread of virus from the inoculum cells to the fresh, uninfected cells.

Cells must rapidly attach to the substratum, but subsequent growth is not required. Cells must be metabolically active for uptake of the infectious virus or vector construct and for efficient elaboration of the product. The ability of the TMA microcarriers to support rapid cell attachment, spreading and growth under serum-free conditions makes this substrate an ideal candidate for both applications.

Summary

An ideal microcarrier should support i) rapid cell attachment and spreading; ii) high-density growth and high metabolic activity; and iii) easy cell detachment. It is critically important that this all be able to occur under serum free conditions as well as in the presence of low serum containing medium. The TMA microcarriers combine these features with low manufacturing costs, long shelf-life and ease of handling. Because of this, these microcarriers will function as a replacement for the dextran-based microcarriers currently provided. As indicated above, the whole biologicals manufacturing industry is on the verge of a major change. Concern over transmission of "slow virus"—type infectious agents through animal products is providing the impetus to move from serum-supported cell growth to growth under serum free conditions. Not coincidentally, a large and growing number of completely-defined culture media are now available for this purpose. The TMA microcarriers will provide the animal product-free substrate for use with these synthetic, animal product-free media.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

Commercially Available Microcarriers

| Type | Company | Tradename | Country of manufacture | Size range available (microns) | Nature of bend | Charged moiety added | Densities available (g/cc) | Autoclavable (121 to 131 C.) | Rehydration required |
|---|---|---|---|---|---|---|---|---|---|
| TMA-polystyrene 2nd embodiment with a t-butyl styrene back bone would lower this | SoloHill SoloHill | Hillex (proposed) | USA | 38 to 300 | rigid | yes | 1.03 to 1.1 1.03 to 1.04 | yes | no |
| Modified polystyrene with coatings and/or surface treatments | | Collagen coated | | 50 to 250 | rigid | no | 0.98 to 1.05 | yes | no |
| | | Glass coated | | 50 to 250 | rigid | no | 0.98 to 1.05 | yes | no |
| | | FACT | | 50 to 250 | rigid | no | 0.98 to 1.05 | yes | no |
| | | Plastic Plus | | 50 to 250 | rigid | no | 0.98 to 1.05 | yes | no |
| | | ProNectin F coated | | 50 to 250 | rigid | no | 0.98 to 1.05 | yes | no |
| Treated dextran | Amersham/ Pharmacia | Cytodex 1, 2 and 3 | Sweden | 150 to 200 | sponge like | yes | 1.03 to 1.04 | yes | yes |
| Treated cellulose | | Cytopore 1 and 2 | | 200 to 280 | macroporous sponge like | yes | 1.03 | yes | yes |
| Polystyrene | Nunc | Biosilon | Denmark | 150 to 250 | rigid | ? | 1.05 | no | no |
| Gelatin | Purcel | Cultisphere | Sweden | 200 to 500 | macroporous | no | 1.04 | yes | yes |

REFERENCES

Ausubel, et al., *Current Protocols in Molecular Biology*, John Wiley and Sons, Baltimore, Md. (1989).

Gebb, et al. (1982). Alternate surface for microcarrier culture of animal cells. *Dev. Biol. Standards.* 50:93–102.

Giard, et al. (1977). Virus production with a newly-developed microcarrier system. *Appl. Environ. Microbiol.* 34:668–672.

Keese, et al. (1983). Cell growth on liquid microcarriers. *Science* 219:1448–1449.

Neilson, et al. (1980) Biosilon: Optimal culture conditions and various research scale culture techniques. *Dev. Biol. Stand.* 46:131–136.

Obrenovitch, et al. (1982). Microcarrier culture of fibroblastic cells on modified trisacryl beads. *Biol. Cell.* 46:249–256.

Sambrook, et al, *Molecular Cloning: A Laboratory Manual*, Cold springs Harbor Laboratory, New York (1989, 1992)

Varani, J., et al., (1983). Growth of three established cell lines on glass microcarriers. *Biotech. Bioengineer* 25:1359–1372.

Varani, et al. (1988). the effect of substrate on the production of infectious virus by cells in culture. *J. Biol. Stand.* 16:333–338.

Varani, et al. (1986). Cell growth on microcarriers: Comparison of proliferation on and recovery from various substrates. *J. Biol. Stand.* 14:331–336.

Varani, et al.(1989). Substrate-dependent differences in production of extracellular matrix molecules by squamous carcinoma cells and diploid fibroblasts. *Biotech. Bioengineer* 33:1235–1241.

Varani, et al. (1993). Use of recombinant and synthetic peptides as attachment factors for cells on microcarriers. *Cytotechnology* 13:89–98.

Van Wezel, A. L. (1967). Growth of cell strains and primary cells on microcarriers. *Nature* 216:65–66.

What is claimed is:

1. A microcarrier bead made of a styrene copolymer core with a tri-methylamine exterior covalently linked to said core, said bead having been washed in basic and acidic solutions thereby making said bead compatible for cell culture.

2. The microcarrier bead according to claim 1, wherein said bead is made of t-butyl styrene back bone with a tri-methylamine exterior.

3. The microcarrier bead according to claim 1, wherein said bead has a diameter in the range of 75–225 μm.

4. The microcarrier bead according to claim 1, wherein said bead has a density in the range of 1.04–1.1 g/cc.

5. A method of using microcarrier beads with a tri-methylamine exterior covalently linked to a styrene core which have been washed with basic acidic solutions for increased growth of anchorage dependent cells including the steps of mixing the microcarrier beads with anchorage dependent cell—containing culture medium and growing cells anchorage dependent on the microcarrier beads to obtain said increased growth of anchorage dependent cells.

6. The method according to claim 5, further including stirring the culture medium continually.

7. The method according to claim 6, further including removing the growth of anchorage dependent cells from the microcarrier bead.

8. The method according to claim 7, wherein said removing step includes washing the microcarrier with a protein dissociating solution.

9. A method of making microcarrier beads comprising the steps of:

forming a bead consisting of a lightly crosslinked styrene copolymer core and having tri-methylamine groups covalently linked to the core on the surface of the core; and washing the microcarrier beads with basic and acidic solutions to make the beads compatible with cell culture.

10. The method according to claim 9, wherein said washing step further includes:

washing the microcarrier beads first with a basic solution;

rinsing the microcarrier beads with deionized water until a neutral pH is reached;

washing the microcarrier beads in an acidic solution;

rinsing the microcarrier beads with water until a neutral pH is reached; and drying the microcarrier beads with air.

11. The method according to claim 10, wherein said rinsing step further includes rinsing the microcarrier beads with deionized water until a neutral pH is reached.

12. The method according to claim 10, wherein said drying step further includes drying with air.

13. The method according to claim 9, further including the step of applying a coating to the microcarrier bead surface.

* * * * *